United States Patent
Plahey et al.

(10) Patent No.: US 11,964,088 B2
(45) Date of Patent: Apr. 23, 2024

(54) VOLUME-BASED PRIMING OF DIALYSIS MACHINES

(71) Applicants: Fresenius Medical Care Holdings, Inc., Waltham, MA (US); Debiotech S.A., Lausanne (CH)

(72) Inventors: Kulwinder S. Plahey, Martinez, CA (US); Pierre Thiebaud, Lausanne (CH); John A. Biewer, Waltham, MA (US)

(73) Assignees: Fresenius Medical Care Holdings, Inc., Waltham, MA (US); Debiotech S.A., Lausanne (CH)

( * ) Notice: Subject to any disclaimer, the term of this patent is extended or adjusted under 35 U.S.C. 154(b) by 143 days.

(21) Appl. No.: 17/861,453

(22) Filed: Jul. 11, 2022

(65) Prior Publication Data

US 2022/0347365 A1    Nov. 3, 2022

Related U.S. Application Data

(63) Continuation of application No. 16/536,618, filed on Aug. 9, 2019, now Pat. No. 11,413,386.

(51) Int. Cl.
*A61M 1/28* (2006.01)
*A61M 1/36* (2006.01)
*G16H 20/17* (2018.01)

(52) U.S. Cl.
CPC .......... *A61M 1/288* (2014.02); *A61M 1/3643* (2013.01); *A61M 2205/50* (2013.01); *G16H 20/17* (2018.01)

(58) Field of Classification Search
CPC ................ A61M 1/288; A61M 1/3643; A61M 2205/3379; A61M 2205/50; G16H 20/17
See application file for complete search history.

(56) References Cited

FOREIGN PATENT DOCUMENTS

JP    2017051423 A    3/2017

*Primary Examiner* — Dirk R Bass
(74) *Attorney, Agent, or Firm* — KDW Firm PLLC

(57) ABSTRACT

A dialysis system may include a dialysis machine (e.g., a peritoneal dialysis machine) having a fluid system for delivering fluid (e.g., dialysate) to a patient. The dialysis machine may include at least one processor and a memory coupled to the at least one processor, the memory comprising instructions that, when executed by the processor, may cause the at least one processor to determine volume information for a fluid system of a dialysis machine, wherein the volume information may comprise a patient line volume and an accuracy adjustment volume, and to determine a priming volume to prime the fluid system with a fluid based on the volume information. Other embodiments are described.

20 Claims, 12 Drawing Sheets

*Volume Patient Line$_{max}$ Low Feature Set 605*

| Tube length | | |
|---|---|---|
| Description | [inch] | [mm] |
| Low spec | 119 | 3022.6 |
| Nominal | 120 | 3048 |
| High spec | 121 | 3073.4 |

X

| Tube diameter | | |
|---|---|---|
| Description | [inch] | [mm] |
| Low spec | 0.153 | 3.9 |
| Nominal | 0.158 | 4.0 |
| High spec | 0.163 | 4.1 |

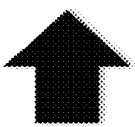

| Patient line volume | |
|---|---|
| Description | [mL] |
| Low spec | 35.9 |
| Nominal | 38.6 |
| High spec | 41.4 |

*Volume Patient Line$_{max}$ Medium/High Feature Set 610*

| Tube length | | |
|---|---|---|
| Description | [inch] | [mm] |
| Low spec | 238 | 6045.2 |
| Nominal | 240 | 6096 |
| High spec | 242 | 6146.8 |

X

| Tube diameter | | |
|---|---|---|
| Description | [inch] | [mm] |
| Low spec | 0.153 | 3.9 |
| Nominal | 0.158 | 4.0 |
| High spec | 0.163 | 4.1 |

| Patient line volume | |
|---|---|
| Description | [mL] |
| Low spec | 71.7 |
| Nominal | 77.1 |
| High spec | 84.1 |

*FIG. 6*

VOLUME-BASED PRIMING OF DIALYSIS MACHINES

This application is a continuation of U.S. patent application Ser. No. 16/536,618, filed Aug. 9, 2019, the entire disclosure of which is incorporated herein by reference in its entirety.

FIELD

The disclosure generally relates to a dialysis system, and more particularly to techniques for priming a dialysis system prior to a dialysis treatment.

BACKGROUND

Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight, without clinical staff in attendance.

A dialysis machine, such as a peritoneal dialysis machine, may include one or more containers (e.g., bags) containing a fluid, for instance, a dialysate, for patient infusion. In PD machines, for example, tubing as one or more fluid lines are inserted into an abdomen of a patient for flowing fresh dialysate and removing used dialysate, waste, and excess fluid. Prior to patient insertion and a dialysis treatment, the tubing is primed with dialysate to minimize air in the tubing being delivered to the peritoneal cavity of the patient, which may cause pain or discomfort.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In accordance with various aspects of the described embodiments is a dialysis machine that may include a memory and at least one processor coupled to the memory. The memory may include instructions that, when executed by the at least one processor, cause the at least one processor to determine volume information for a fluid system of a dialysis machine, the volume information may include a patient line volume and an accuracy adjustment volume, and determine a priming volume to prime the fluid system with a fluid based on the volume information. The dialysis machine may be a peritoneal dialysis machine.

In some embodiments of the dialysis machine, the dialysis machine may further include a pump, the instructions, when executed by the at least one processor, may cause the at least one processor to prime the fluid system by causing the pump to pump the priming volume of the fluid into the fluid system.

In various embodiments of the dialysis machine, the patient line volume may include a maximum volume for a fluid system configuration. In exemplary embodiments of the dialysis machine, the fluid system configuration may be associated with at least one dimension of at least one component of the fluid system. In various embodiments of the dialysis machine, the fluid system may include a set of patient line tubing, and the fluid system configuration may be associated with a length and a diameter of the set of patient line tubing. In some embodiments of the dialysis machine, the accuracy adjustment volume may be associated with a volume measurement error for measuring a volume of the fluid required to fill the fluid system.

In exemplary embodiments of the dialysis machine, the instructions, when executed by the at least one processor, may cause the at least one processor to determine the priming volume according to: priming volume=volume patient line$_{max}$+accuracy adjustment$_{max}$. In various embodiments of the dialysis machine, the fluid system may include non-primed elements, the instructions, when executed by the at least one processor, may cause the at least one processor to determine the priming volume according to: priming volume=volume patient line$_{max}$+accuracy adjustment$_{max}$−volume non-primed elements.

In some embodiments of the dialysis machine, the volume information may include system element information to indicate a volume of the fluid system from non-patient line elements of the fluid system. In various embodiments of the dialysis machine, the priming volume may include a worst-case volume of fluid required to prime a configuration of the fluid system.

In accordance with various aspects of the described embodiments is a method for priming a fluid system of a dialysis machine. The method may include determining volume information for a fluid system of a dialysis machine, the volume information may include a patient line volume and an accuracy adjustment volume, and determining a priming volume to prime the fluid system with a fluid based on the volume information. The dialysis machine may be a peritoneal dialysis machine.

In some embodiments of the method, the method may include priming the fluid system by causing a pump to pump the priming volume of the fluid into the fluid system. In various embodiments of the method, the patient line volume may include a maximum volume for a fluid system configuration. In exemplary embodiments of the method, the fluid system configuration may be associated with at least one dimension of at least one component of the fluid system. In some embodiments of the method, the fluid system may include a set of patient line tubing, the fluid system configuration may be associated with a length and a diameter of the set of patient line tubing. In various embodiments of the method, the accuracy adjustment volume may be associated with a volume measurement error for measuring a volume of the fluid required to fill the fluid system.

In some embodiments of the method, the priming volume may be determined according to: priming volume=volume patient line$_{max}$+accuracy adjustment$_{max}$. In various embodiments of the method, the priming volume may be determined according to: priming volume=volume patient line$_{max}$+accuracy adjustment$_{max}$—volume non-primed elements.

In exemplary embodiments of the method, the volume information may include system element information that may indicate a volume of the fluid system from non-patient line elements of the fluid system. In various embodiments of the method, the priming volume may include a worst-case volume of fluid required to prime a configuration of the fluid system.

BRIEF DESCRIPTION OF THE DRAWINGS

By way of example, specific embodiments of the disclosed machine will now be described, with reference to the accompanying drawings, in which:

FIG. 6 illustrates exemplary volume patient line determinations in accordance with the present disclosure;

DETAILED DESCRIPTION

Figure 1:
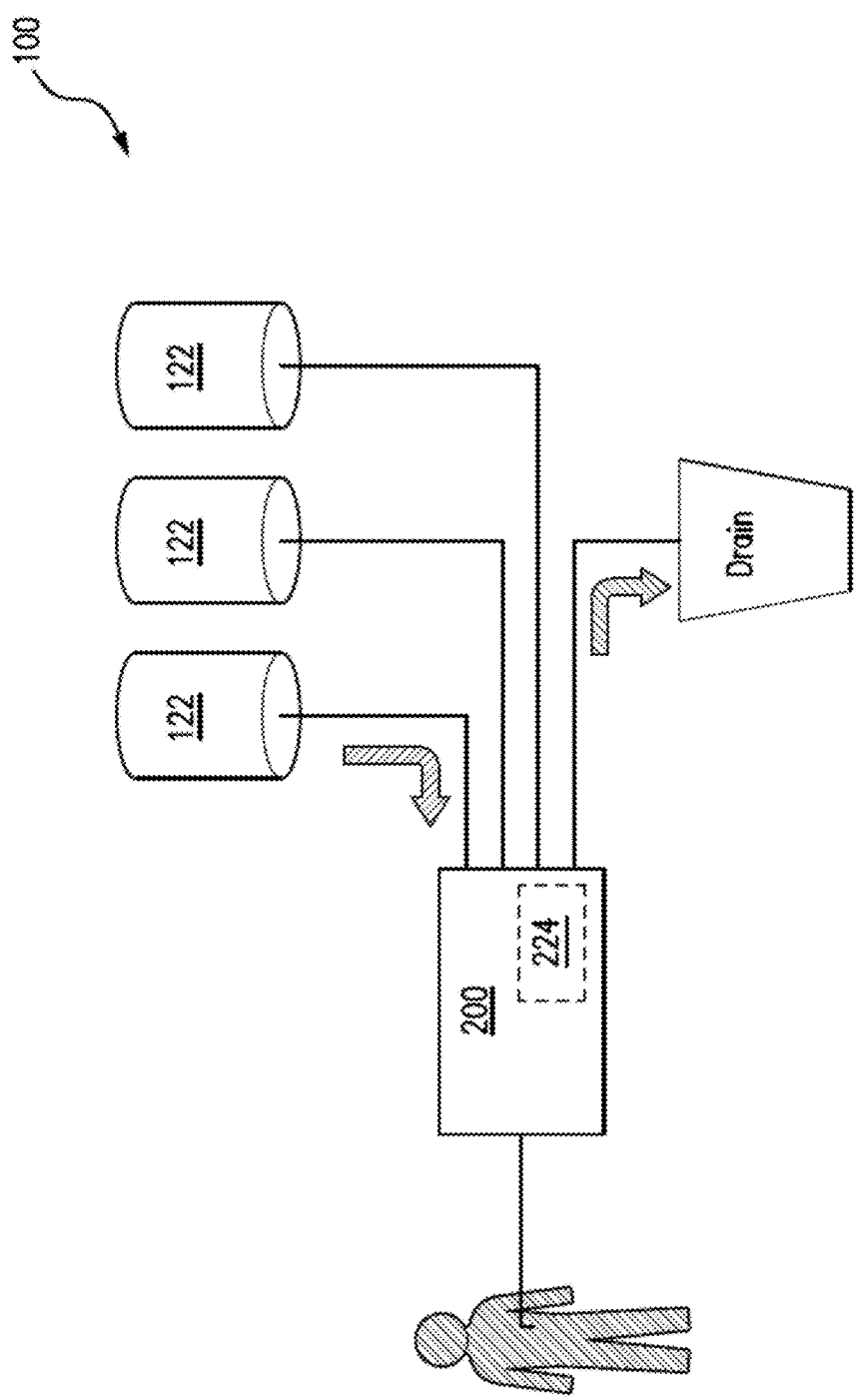
FIG. 1 illustrates an exemplary embodiment of a dialysis system configured in accordance with the present disclosure.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

As described above, in peritoneal dialysis operations, a fluid system is connected between a dialysis machine and a patient for delivering fresh dialysate into the patient's peritoneal cavity and removing used dialysate and contaminants after a predetermined time. A patient may undergo several cycles of delivery of fresh dialysate and removal of the used dialysate and contaminants in a single treatment. In some embodiments, a peritoneal dialysis treatment may be performed at home, and may occur overnight while a patient is sleeping.

Tubing is primed when a fluid (e.g., dialysate) is pumped or otherwise forced through the tubing, for example, prior to being inserted in the patient, to reduce, or even completely eliminate, air present in the tubing. Priming minimizes or prevents air infusion to the peritoneal cavity of the patient, thereby minimizing potential pain, cramps, and/or other discomfort during the dialysis treatment. In addition, removal of air via priming may minimize or eliminate air detection alarms in systems having air detection functionality.

Semi- or fully-automated priming checks may generally include a timer in the dialysis machine, so that fluid is flowed through the tubing for a predetermined time period, which may align with a length of the tubing. Additionally, pressure sensors and/or programmed volume verifications may be used, although these typically require direct contact with the fluid. Certain systems may prime with a given volume of solution. However, such systems according to conventional techniques do not account for all of the variables that may affect priming volume, such as system inaccuracies, tubing properties (for instance, tubing inner diameter, tubing length, and/or the like), measurement errors, and/or the like. In addition, such systems according to conventional techniques may be biased toward using a smaller volume to avoid generating pressure during priming (for instance, to avoid over-priming), because the systems do not have a tolerance (or a sufficient tolerance) for a pressure increase caused by using a greater volume for priming than required to remove air from the tubing. Other systems may use an air detector, for example, on a patient line to detect when fluid has reached the correct position to indicate the system is primed. However, in some cases, a patient (or an automated system) may not know if the tubing was properly connected (e.g., whether the patient line connector was properly positioned in the sensor) and/or it may be unclear whether all patient loading steps and checks were performed to ensure proper sensor positioning.

Exemplary embodiments of the present disclosure provide techniques for volume-based priming of a dialysis system. In some embodiments, a dialysis system may operate to determine a priming volume of a dialysis machine fluid system, such as tubing and/or other elements used to deliver fluid (e.g., dialysate) to a patient. The priming volume may be based on volume information associated with the fluid system of the dialysis system, such as tubing information (for instance, properties affecting the volume of fluid that may be arranged within the tubing), system elements information (for instance, properties affecting the volume of fluid that may be arranged within fluid containers, warming elements, and/or the like), accuracy information (for instance, determined measurement accuracy for a system), and/or the like.

In some embodiments, the priming volume may include the maximum volume of fluid that may be arranged in the fluid system, taking into account, among other potential factors, different fluid system component properties and fluid volume measurement accuracy. Accordingly, in exemplary embodiments, the priming volume may be or may be associated with a "worst-case" volume requirement (for instance, the maximum amount) of fluid required to prime the system, including among different configurations (e.g., lengths) of tubing sets that may be compatible with the system. In this manner, a patient may be assured that the system will be primed as all or essentially all volume scenarios are accounted for as the priming volume extends out to the maximum, worst-case requirement. In certain configurations, the priming volume may be greater than the actual volume required to prime the system, and pressure may build up in the fluid system due to over-priming. As described in more detail below, systems according to some embodiments may include elements (for instance, filters, fluid containers, and/or the like) that may tolerate the pressure (for instance, without being damaged, leaking, false alarming (e.g., falsely indicating an occlusion or other blockage in the system due to overpressure) and/or the like) and/or expand or otherwise deform to manage a pressure increase.

Accordingly, some embodiments may provide technological advantages over conventional systems, including improvements in computing technology (for instance, computing systems operative to control or otherwise manage dialysis systems). One non-limiting example of a technological advantage is providing more accurate and efficient priming of dialysis systems, for example, that minimizes patient involvement to verify sufficient priming. In a further non-limiting example of a technological advantage, embodiments may provide a volume-based (not pressure-based) priming process capable of effectively priming various types and lengths of fluid systems. Embodiments are not limited in this context.

Figure 2:
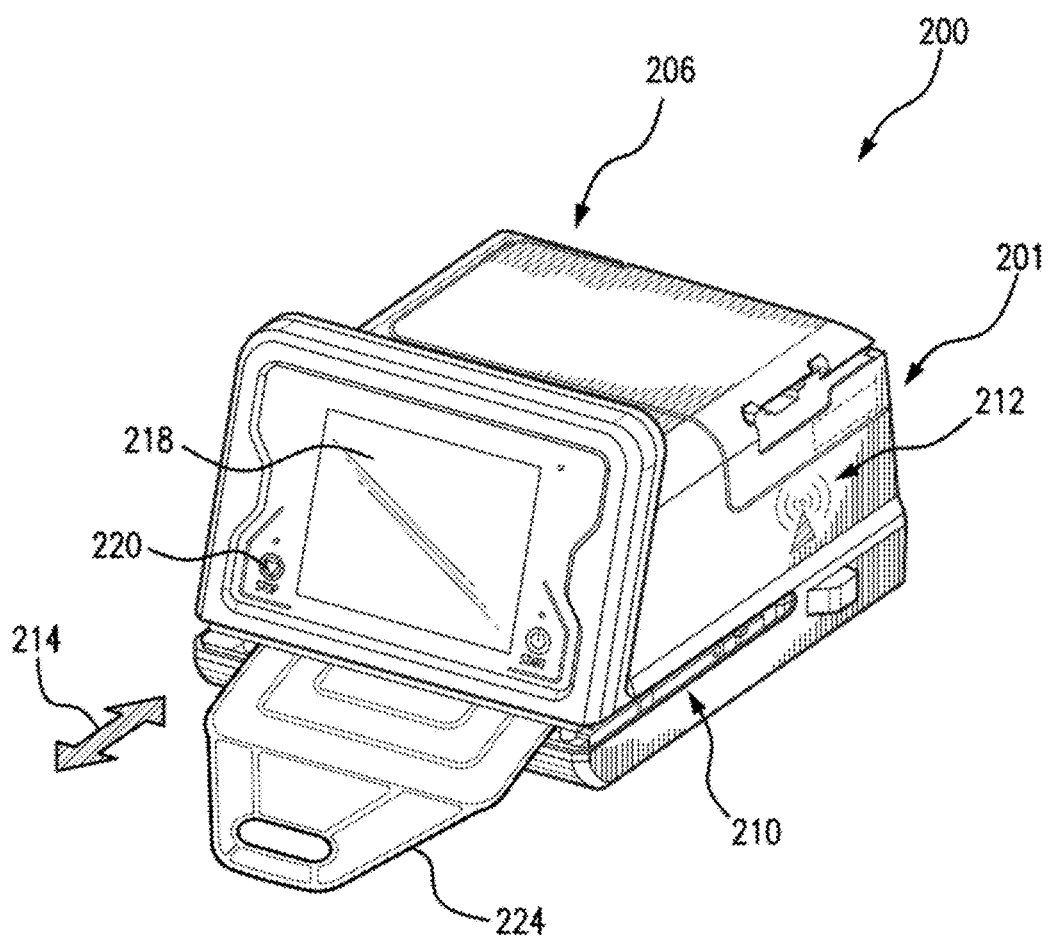
FIG. 2 illustrates an exemplary embodiment of a dialysis machine in the dialysis system of FIG. 1 in accordance with the present disclosure.

Referring to FIGS. 1-2, a dialysis system 100 may include a peritoneal dialysis machine 200, for flowing fresh dialysate into a patient and draining used dialysate out of the patient. During treatment, a volume of dialysate may enter the patient's abdomen and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the used dialysate may flow out of the patient's abdomen and be purged to a drain connected to the tubing, e.g., the drain line. This exchange of fresh dialysate and used dialysate after a dwell time may occur for several cycles depending on the patient's treatment regimen.

Dialysate bags 122 may be connected to the dialysis machine 200. Valves may be attached to a bottom portion of the dialysate bags 122 so fluid is drawn out and air delivery is minimized. Dialysate from the dialysate bags 122 may be heated using a warmer pouch 224. When the dialysis system 100 has been primed according to some embodiments and dialysate has reached a predetermined temperature (e.g., approximately 98°–100° F., 37° C.), the dialysate may be moved into the patient. The dialysate bags 122 and/or the warmer pouch 224 may be connected to a cassette, which may be insertable into the dialysis machine 200. In addition, a patient line and a drain line may be connected to the cassette. The patient line may be connected to a patient's abdomen via a catheter and may be used to pass dialysate to the patient's peritoneal cavity during use. The drain line may be connected to a drain or drain receptacle and may be used to drain dialysate during a treatment.

Although peritoneal dialysis and peritoneal dialysis machines are used in some examples herein, embodiments are not so limited, as any fluid system (including any dialysis system) requiring priming that may operate according to the volume-based priming processes of some embodiments is contemplated herein.

FIG. 2 illustrates an exemplary embodiment of a dialysis machine 200 in dialysis system 100 in accordance with the present disclosure. The dialysis machine 200 may be implemented in the dialysis system 100 and may include, for example, a housing 206, a processing module 201, a connection component 212, a touch screen 218, and a control panel 220 operable by a user (e.g., a caregiver or a patient) to allow, for example, set up, initiation, and/or termination of a dialysis treatment.

The touch screen 218 and the control panel 220 may allow a user to input various treatment parameters or other information (for instance, fluid system model numbers, characteristics (for example, length, diameter, and/or the like), and/or the like) to the dialysis machine 200 and to otherwise control the dialysis machine 200. In addition, the touch screen 218 may serve as a display. The touch screen 218 may function to provide information to the patient and the operator of the dialysis system 100. For example, the touch screen 218 may display information related to a dialysis treatment to be applied to the patient, including information related to a prescription.

The dialysis machine 200 may include a processing module 201 (see, for example, FIG. 5 for illustrative processing circuitry) that resides inside the dialysis machine 200 or is otherwise operably coupled to the dialysis machine 200, the processing module 201 may be configured to communicate with the touch screen 218 and the control panel 220. The processing module 201 may be configured to receive data from the touch screen 218 the control panel 220 and sensors, e.g., air, temperature and pressure sensors, and control the dialysis machine 200 based on the received data. For example, the processing module 201 may adjust the operating parameters of the dialysis machine 200.

The dialysis machine 200 may be configured to connect to a network. The connection to the network may be via a wired and/or wireless connection. The dialysis machine 200 may include a connection component 212 configured to facilitate the connection to the network. The connection component 212 may be a transceiver for wireless connections and/or another signal processor for processing signals transmitted and received over a wired connection. Other medical devices (e.g., other dialysis machines) or components may be configured to connect to the network and communicate with the dialysis machine 200.

One or more heating elements may be disposed internal to the machine 200. For example, the warmer pouch 224 may be insertable into an opening 210 in a direction indicated at arrow 214. In embodiments, the warmer pouch 224 may be configured so dialysate may continually flow through the warmer pouch 224 to achieve a predetermined temperature before flowing into the patient. For example, in some embodiments the dialysate may continually flow through the warmer pouch 224 at a rate of approximately 200 mL/min. Internal heating elements (not shown) may be positioned above and/or below the opening 210, so that when the warmer pouch 224 is inserted into the opening 210, the one or more heating elements may affect the temperature of dialysate flowing through the warmer pouch 224. In some embodiments, an internal warmer pouch may instead be a portion of tubing in the system that is passed by, around, or otherwise configured with respect to, a heating element(s). In some embodiments, a dialysis machine 200 may provide an active measurement of the dialysate temperature in dialysate bags and/or warmer pouches, e.g., in the dialysate bags 122, and the warmer pouch 224 of FIGS. 1-2. It is understood that FIGS. 1-2 illustrate dialysate continuously flowing through the warmer pouch 224 "in-line" with the dialysis machine 200, reaching an acceptable temperature by the application of internal heating elements. As described herein, prior to insertion of the patient line into the patient, the tubing may be primed with fluid (e.g., dialysate), to purge air from the tubing.

Figure 3:
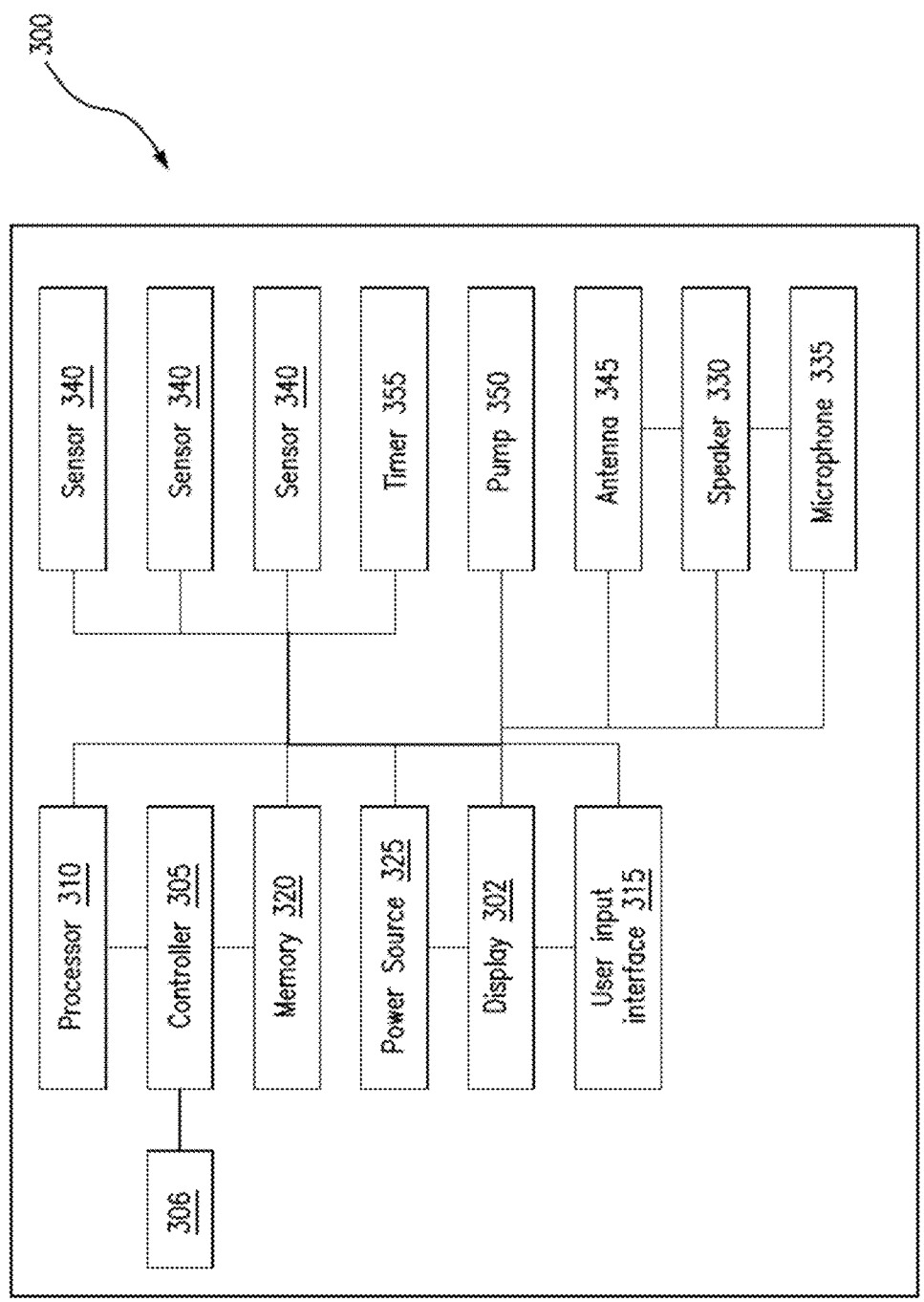
FIG. 3 is a block diagram illustrating an exemplary embodiment of a dialysis machine controller in accordance with the present disclosure.

Referring to FIG. 3, a schematic of an exemplary embodiment of a dialysis machine 300 and a controller 305 (see, for example, FIG. 5) in accordance with the present disclosure are shown. The machine 300 may be a home dialysis machine, e.g., a peritoneal dialysis machine, for performing a dialysis treatment on a patient, and may be included in the system 100 described above with respect to FIGS. 1-2 and dialysis machine 200. The controller 305 may automatically control execution of a treatment function, including a volume-based priming process, during a course of dialysis treatment. The controller 305 may be operatively connected to sensors 340 and deliver a signal to execute a treatment function (e.g., transferring dialysate from the dialysate bag 122 through the warmer pouch 224 and then to the patient), or a course of treatment associated with various treatment systems. In some embodiments, a timer 355 may be included for timing triggering of sensors 340.

In some embodiments, the controller 305, processor 310, and/or memory 320, or combinations thereof of the machine 300 may receive sensor 340 signals indicating a dialysate air content. Each fluid bag (e.g., the dialysate bags 122) may contain an approximate amount of dialysate, such that "approximate amount" may be defined as a 3 L fluid bag containing 3000 to 3150 mL, a 5 L fluid bag containing 5000 to 5250 mL, and a 6 L fluid bag containing 6000 to 6300 mL. The controller 305 may also detect connection of all fluid bags 122 connected. As described above, each fluid bag 122 may contain some amount of air, which may change over time.

Communication between the controller 305 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to prime system, trigger pump to deliver dialysate, and/or the like) and a status associated with specific operations (e.g., ready to execute, priming, primed, executing, completed, successfully completed, queued for execution, waiting for control signal, and/or the like).

In various embodiments, the dialysis machine 300 may include at least one pump 350 operatively connected to the controller 305. During a treatment operation, which may be or may include a volume-based priming process according to some embodiments, the controller 305 may control the pump 350 for pumping fluid, e.g., fresh and spent dialysate, to and from a patient. The pump 350 may also pump dialysate from the dialysate bag 122 through the warmer pouch 224. The controller 305 may also be operatively connected to a speaker 330 and a microphone 335 disposed in the machine 300. The user input interface 315 may include a combination of hardware and software components that allow the controller 305 to communicate with an external entity, such as a patient or other user. These components may be configured to receive information from actions such as physical movement or gestures and verbal intonation. In embodiments, the components of the user input interface 315 may provide information to external entities. Examples of the components that may be employed within the user input interface 315 include keypads, buttons, microphones, touch screens, display screens, and speakers. The machine 300 may also be wirelessly connectable via the antenna 345 for remote communication.

As shown in FIG. 3, sensors 340 may be included for monitoring parameters and may be operatively connected to at least the controller 305, processor 310, and/or memory 320, or combinations thereof. The processor 310 may be configured to execute an operating system, which may provide platform services to application software, e.g., for operating the dialysis machine 300. These platform services may include inter-process and network communication, file system management and standard database manipulation. One or more of many operating systems may be used, and examples are not limited to any particular operating system or operating system characteristic. In some examples, the processor 310 may be configured to execute a real-time operating system (RTOS), such as RTLinux, or a non-real time operating system, such as BSD or GNU/Linux.

The memory 320 (see, for example, FIG. 5) may include a computer readable and writeable nonvolatile data storage medium configured to store non-transitory instructions and data. In addition, the memory 320 may include a processor memory that stores data during operation of the processor 310. In some examples, the processor memory may include a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 320 may include executable programs or other code that may be executed by the processor 310. The instructions may be persistently stored as encoded signals, and the instructions may cause the processor 310 to perform the functions described herein. The memory 320 may include information that is recorded, on or in, the medium, and this information may be processed by the processor 310 during execution of instructions. The memory 320 may also include, for example, specification of data records for user timing requirements, timing for treatment and/or operations, historic sensor information, and the like (see, for example, FIG. 5). The medium may, for example, be optical disk, magnetic disk or flash memory, among others, and may be permanently affixed to, or removable from, the controller 305.

A pressure sensor may be included for monitoring fluid pressure of the machine 300, although the sensors 340 may also include other types of sensors, such as a temperature sensor and/or a weight sensor. It is appreciated that the sensors 340 may include sensors with varying sampling rates, including wireless sensors.

The controller 305 may be disposed in the machine 200, 300 or may be coupled to the machine 200, 300 via a communication port or wireless communication links, shown schematically as communication element 306 (see FIG. 3). According to various examples, the communication element 306 may support a variety of one or more standards and protocols, examples of which include USB, WiFi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 300, the controller 305 may be operatively connected to any of the sensors 340, pump 350, and the like. The controller 305 may communicate control signals or triggering voltages to the components of the machine 300. As discussed, exemplary embodiments of the controller 305 may include wireless communication interfaces. The controller 305 may detect remote devices to determine if any remote sensors are available to augment any sensor data being used to evaluate the patient.

Figure 4:
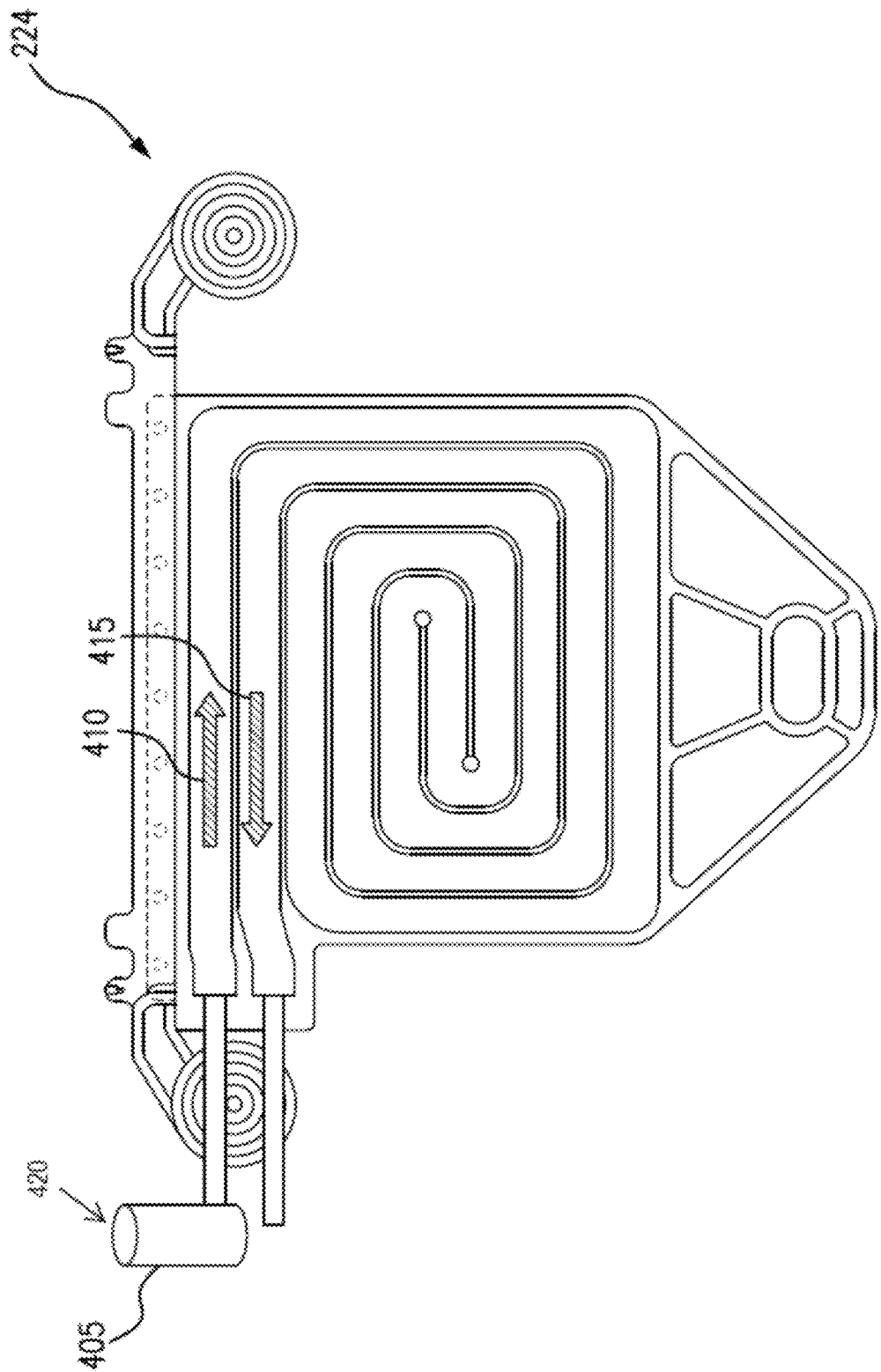
FIG. 4 illustrates an exemplary embodiment of a warmer pouch for the dialysis system of FIG. 1 in accordance with the present disclosure.

As shown in FIG. 4, the warmer pouch 224 may include a filter 405 in-line with warmer pouch 224, e.g., coupled to an inlet of the warmer pouch 224. For example, dialysate flowing to the patient through the warmer pouch 224 from dialysate bags 122 may flow through the filter 405, e.g., before entering the warmer pouch 224. In embodiments, the filter 405 may be coupled to the warmer pouch 224 directly or indirectly by tubing. The filter 405 may filter out air content in the dialysate flow. In some embodiments, the filter 405 may be a container 420, e.g., a cylindrical container, having an inlet for receiving dialysate and air, and an outlet for flowing dialysate with air content filtered out of the dialysate. It is understood that the container 420 may be any configuration, e.g., size and/or shape, to filter air content from dialysate. In some embodiments, the filter 405 may be arranged as part of a patient connector (for instance, as part of a cap of the patient connector). In various embodiments, a filter in addition to filter 405 may be arranged as part of a patient connector. For example, warmer pouch 224 may include a hydrophobic filter (not shown) at the end of the patient line through which air may be expelled during priming.

Dialysate may flow through the filter 405 at the inlet of the warmer pouch 224 and may flow through an extended flow path in the warmer pouch 224. For example, a flow path may be a tortuous, or circuitous, pathway, so that the dialysate may flow at a constant rate into the patient and may heat to the desired predetermined temperature while flowing through the tortuous flow path of the warmer pouch 224. The dialysate may flow from the warmer pouch into the patient at an outlet of the warmer pouch 224, indicated at arrow 415. Although the flow path shown in FIG. 4 is somewhat circular, any labyrinth of circuitous flow path may be incorporated in the warmer pouch 224 to ensure a constant flow of the dialysate so that the dialysate temperature is heated to the predetermined temperature before flowing into the patient.

As described above, the dialysis machine 200 may include in-line heating of the dialysate via the warmer pouch 224. The filter 405 may also be disposed in-line with the warmer pouch 224, which may always be in a positive pressure relative to ambient on the outlet of the pump and between the pump and the patient. In some embodiments, at least a portion of the warmer pouch may be compliant, for example, able to undergo elastic deformation when subjected to an applied force. Accordingly, as described according to some embodiments having a warmer pouch, if pressure builds up during priming, at least a portion of the pressure may be reduced by compliance of the warmer pouch.

Figure 5:
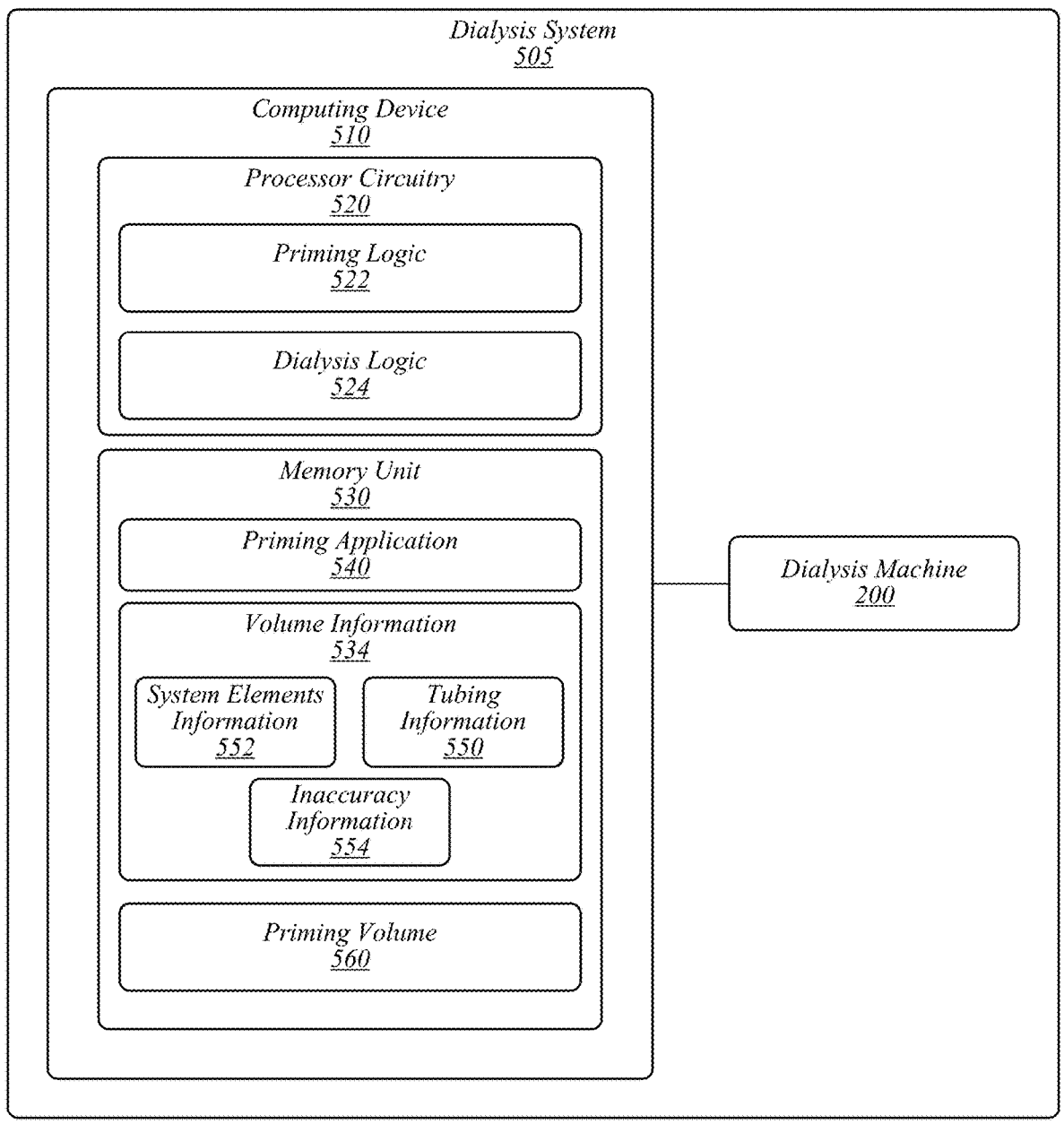
FIG. 5 illustrates an exemplary operating environment in accordance with the present disclosure.

FIG. 5 illustrates an example of an operating environment 500 that may be representative of some embodiments. As shown in FIG. 5, the operating environment 500 may include a dialysis system 505 associated with a dialysis machine 200. In various embodiments, the dialysis system 505 may include a computing device 510 communicatively coupled to the dialysis machine 200. The computing device 510 may be operative to manage, among other things, a volume-based priming process associated with the dialysis machine 200.

Although only one computing device 510 and dialysis machine 200 are depicted in FIG. 5, embodiments are not so limited. In various embodiments, the functions, operations, configurations, data storage functions, applications, logic, and/or the like described with respect to the computing device 510 may be performed by and/or stored in one or more other computing devices (not shown), for example, coupled to the computing device 510 via a network. A single computing device 510 and dialysis machine 200 are depicted for illustrative purposes only to simplify the figure. For example, the computing device 510 may operate to partially or wholly operate a volume-based priming process for a plurality of dialysis machines 200 coupled to the computing device 510, for instance, via a network. Embodiments are not limited in this context.

The computing device 510 may include a processor circuitry 520 communicatively coupled to a memory unit 530. The processing circuitry 520 may be or may include processing module 201 and/or controller 305. The processor circuitry 520 may include and/or may access various logic for performing processes according to some embodiments. For instance, the processor circuitry 520 may include and/or may access a priming logic 522 and/or a dialysis logic 524. The processing circuitry 520, the priming logic 522, and/or the dialysis logic 524, and/or portions thereof, may be implemented in hardware, software, or a combination thereof. As used in this application, the terms "logic," "component," "layer," "system," "circuitry," "decoder," "encoder," and/or "module" are intended to refer to a computer-related entity, either hardware, a combination of hardware and software, software, or software in execution, examples of which are provided by the exemplary computing architecture 1100. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although the priming logic 522 and the dialysis logic 524 are depicted in FIG. 5 as being within the processor circuitry 520, embodiments are not so limited. For example, the priming logic 522, the dialysis logic 524, and/or any component thereof, may be located within an accelerator, a processor core, an interface, an individual processor die, implemented entirely as a software application (for instance, a priming application 540) and/or the like.

The memory unit 530 (see also, memory 320 of FIG. 3) may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, the memory unit 530 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

The memory unit 530 may store a priming application 540 that may operate, alone or in combination with the priming logic 522 and/or the dialysis logic 524, to control or otherwise manage various operational aspects of the dialysis machine 200. For example, the priming logic 522 may operate to perform volume-based priming processes according to some embodiments. In another example, the dialysis logic 524 may operate to perform a dialysis process (for instance, a peritoneal dialysis process) via the dialysis machine 200.

In some embodiments, memory unit 530 may store volume information 534 used, for example, to determine a priming volume for volume-based priming processes according to various embodiments. The volume information 534 may include tubing information 550 associated with tubing (for instance, patient line tubing) used to deliver fluid from the dialysis machine 200 to a patient. In general, tubing information 550 may include any information that may be used to determine a volume of fluid that may be arranged within the tubing, for instance, when primed (i.e., in the absence of air within the tubing). Non-limiting examples, of tubing information 550 may include tube length, tube inner diameter, tube outer diameter, tube material, tube compliance, tube volume calculations, tubing tolerances, and/or the like.

In some embodiments, the priming logic 522 may determine at least a portion of the tubing information 550 based on operator input. For example, an operator may input certain tubing characteristics, such as tube length, diameter, feature set information, and/or the like. In another example, an operator may input a tubing identifier (for instance, a manufacturer product identifier) and the priming logic 522 may determine at least a portion of the tubing information 550 based on available data associated with the tubing identifier (for instance, via a manufacturer database, an operator database, and/or the like). In a further example, an operator may create predefined configurations, such as "short-low features with patient hub," that may include predefined information defining tubing information 550. In a further example, the dialysis machine 200 may be operative to automatically determine the type of tubing set, for instance, by reading, scanning, or otherwise obtaining information about a tubing set. Embodiments are not limited in this context.

Although various dimensions and related terms (for instance, "long," "short," "low feature," "high feature," and the like) are used in this Detailed Description, embodiments are not so limited, as such dimensions and terms are used for explanatory purposes only. In particular, volume-based priming processes may operate with any dimensions capable of working according to some embodiments. In general, "short" tubing may be about 3 meters (m) and "long" tubing may be about 6 m. However, in some embodiments, tubing may be about 0.10 m, about 0.25 m, about 0.5 m, about 1.0 m, about 2.0 m, about 4.0 m, about 6.0 m, about 10.0 m, about 15.0 m, about 20.0 m, about 25.0 m, about 50.0 m, about 100.0 m, and any range or value between any two of these values (including endpoints). Embodiments are not limited in this context.

In various embodiments, the volume information 534 may include system element information 552 associated with elements of the dialysis system 200 that may hold or otherwise contact fluid that do not include patient line tubing (for instance, non-patient line elements). Non-limiting examples of elements may include bags and other fluid containers, cartridges, hubs (for instance, a patient hub of a cartridge), and/or the like. For example, for a patient hub in a cartridge, the volume may be patient hub volume+patient pressure sensor (PPS) volume. In various embodiments, the tubing information 550 and the system elements information 552 may provide the fluid volume for the fluid system of the dialysis machine 200. In general, the fluid system of the dialysis machine 200 may include the components used to store or facilitate the flow of fluid from the dialysis machine 200 to the patient including, without limitation, conduit, tubing, hubs, cassettes, pouches, and/or the like. In various embodiments, the fluid system may be or may include the components of the dialysis machine 200 that require priming.

In exemplary embodiments, volume information 534 may include inaccuracy (or error) information or accuracy adjustment information 554 associated with the dialysis machine 200 and/or components thereof. In general, accuracy adjustment information 554 may include information indicating the inaccuracy (for instance, tolerance, deviations, errors, and/or the like) or adjustments of fluid volume measurements associated with the dialysis machine 200. In this manner, volume-based priming processes may account for variances in dialysis machines 200 and/or components thereof (for instance, cyclers, warmers, disposable tubing sets, and/or the like), component positioning (for instance, fluid bag heights, drain heights, patient line heights, connector heights, and/or the like), and/or other configuration variables. For example, at least a portion of the warmer pouch may be compliant, for instance, able to undergo elastic deformation when subjected to an applied force (e.g., being filled with a fluid). Certain of the inaccuracy or measurement errors may be due to warmer pouch compliance. In various embodiments, accuracy adjustment information 554 may be a percentage (e.g., percentage of expected priming volume). In other embodiments, accuracy adjustment information 554 may be a value, such as a number of volume units (for instance, 10 mL). In some embodiments, accuracy adjustment information 554 may be determined via one or more experiments, via manufacturer information, dialysis machine information databases, and/or the like (see, for example, FIG. 7). Embodiments are not limited in this context.

In some embodiments, a priming volume 560 may be generated by priming logic 522 based on at least a portion of the volume information to indicate a volume of fluid (e.g., dialysate) to prime the dialysis system to remove or substantially remove air in the fluid system used to move fluid during dialysis. In various embodiments, the priming volume 560 may include a plurality of priming volumes, each for various configurations (e.g., a specific dialysis machine, a short/long tube set with a low/medium/high feature set, a specific warmer pouch, a specific dialysis fluid, and/or the like). In some embodiments, the corresponding priming volume may be selected by an operator or automatically by priming logic 522 based on volume information 534 (such as tubing information). For example, an operator may indicate that a "short" (for instance, 3 meters (m) or less) patient line tubing is being used. Priming logic 522 may select (or recommend for selection by the operator) a corresponding "short" priming volume 560 configured to prime the dialysis machine 200 fluid system with tubing of 3 m or less.

In exemplary embodiments, the priming volume 560 may represent a maximum volume (a worst-case volume) of fluid that needs to be pumped through the fluid system of the dialysis machine 200 to prime the system regardless of the specifics of the fluid system (e.g., a volume sufficient to prime any compatible tubing set, warmer pouch, etc., or the like, suitable for use in or with a particular dialysis machine). For example, some embodiments may determine a "long" priming volume 560 for "long" tube sets (for instance, about 6 meters (m) or longer). In another example, various embodiments may determine a "short" priming volume 560 for "short" tube sets (for instance, about 3 m or less than 6 m). In a further example, various embodiments may determine a "product" priming volume for a specific product identifier. Embodiments are not limited in this context. Accordingly, various configurations should be able to achieve a primed condition using the priming volume 560 because the priming volume includes a volume of fluid required to prime the largest-volume configuration.

In a "best-base" scenario, with the lowest volume (for instance, lowest patient line volume), the fluid system (or at least a portion thereof) may be "over-primed" due to the additional fluid. For example, for a high feature set (see, for example, FIG. 6), an "over-primed" condition may occur with a volume greater than about 90.6 mL and/or a maximum pressure of about 293 mbar. However, in some embodiments, compliance of certain portions of the fluid system (such as the warmer pouch) may accommodate the additional fluid without or with a minimum pressure increase (for instance, a pressure below a threshold to cause the fluid system to leak and/or alarm). In various embodiments, the pressure increase in a best-case scenario may be determined and components (for instance, filters, valves, and/or the like) capable of withstanding this pressure increase may be used in the fluid system of the dialysis machine 200, for example, without damage or leaking fluid through connectors (for instance, patient connectors) or other components. For example, the fluid system and/or components thereof (for instance, filters, valves, and/or the like) may be configured to withstand about 100 mbar, about 200 mbar, about 300 mbar, about 400 mbar, about 500 mbar, and any value or range between any two of these values (including endpoints). In some embodiments, priming (including over-priming conditions) via a volume-based priming process may generate pressures within portions of the fluid system of about 50 mbar to about 300 mbar. After pressure equalization (see, for example, FIG. 10), the pressure may be reduced to about 40 mbar to about 100 mbar.

In some embodiments, the volume information 534 may include maximum pressures of various system components, such as filters (e.g., filter 405), above which the component may be damaged, not operate correctly, or otherwise be negatively affected. For example, the volume information 534 may include pressure rating information for filters and/or other components of the dialysis machine 200. In various embodiments, priming logic 522 may determine a maximum priming pressure that may be generated by priming the fluid system to the priming volume 560. For example, priming logic may determine the maximum priming pressure that may be generated if the "worst-case" priming volume 560 is pumped into the "best-case" (i.e., smallest volume) fluid system. In exemplary embodiments, priming logic 522 may trigger an over-pressure event if the maximum priming pressure is determined to be over the maximum pressure for a component of fluid system. Non-limiting examples of over-pressure events may include generating an alarm, aborting a volume-based priming processes, and/or the like. In some embodiments, an operator may override an over-pressure event. Embodiments are not limited in this context.

In various embodiments, the priming volume 560 may be determined according to the following:

$$\text{priming volume} = \text{volume patient line}_{max} + \text{accuracy adjustment}_{max} \quad \text{(Eq. 1)}.$$

In various embodiments, the volume patient line$_{max}$ may include the maximum volume of the patient tubing line and/or other fluid system components that need to be primed during the volume-based priming process. For example, in some embodiments, the volume patient line$_{max}$ may include the tubing of the fluid system. In another example, the volume patient line$_{max}$ may include the tubing and portions of a cartridge, such as a patient hub in the cartridge (for instance, about 2 mL, based on, for example, a hub volume of 1.83 mL and a PPS volume of 0.12 mL), if applicable.

In some embodiments, certain portions of the fluid system may not be or may not need to be primed via a volume-based priming process ("non-primed elements") (although they may be primed using other priming processes). For example, a warming pouch may be primed using a separate pouch priming process. Accordingly, the volume of the non-primed elements, such as a warming pouch, may be removed from the priming volume determination. In such embodiments, the priming volume 560 may be determined according to the following:

$$\text{priming volume} = \text{volume patient line}_{max} + \text{accuracy adjustment}_{max} - \text{volume non-primed elements} \quad \text{(Eq. 2)}$$

For example, in various embodiments having a warming pouch (see, for example, FIG. 2), the priming volume 560 may be determined according to the following:

$$\text{priming volume} = \text{volume patient line}_{max} + \text{accuracy adjustment}_{max} - \text{volume pouch}_p \quad \text{(Eq. 3)},$$

where p is the pressure of the pouch (for example, about 40 mbar). In some embodiments, the pressure of the pouch for equation (3) may be about 40 mbar, with a low feature set volume of about 5.4 milliliters (mL) and a high feature set of about 6.1 mL. See, for example, FIG. 6 for information associated with determining Equations 1 and/or 2.

FIG. 6 depicts illustrative volume patient line$_{max}$ determinations according to some embodiments. As shown in FIG. 6, a volume patient line$_{max}$ determination may be generated for a low feature set 605 and/or a medium/high feature set 610. Accordingly, the priming volume may be determined for various configurations, classes, or other types of fluid system components, such as tubing with a low feature set, a medium feature set, and/or a high feature set. In various embodiments, volume patient line$_{max}$ may be about 35.9 mL, about 38.6 mL, or about 41.4 mL for a low feature set of tubing. A full patient line error value (see, for example, FIG. 8) may be the difference between the lowest patient line volume and the highest patient line volume. For the example depicted in FIG. 6, the full patient line error for the low feature set may be 41.4 mL-35.9 mL=5.5 mL. In some embodiments, therefore, the volume-based priming process may use the worst-case volume of 41.4 mL to determine the priming volume. In this manner, non-worst-case tubing sets of 35.9 mL and 38.6 mL will be primed because they will require less fluid for priming than the worst-case volume of 41.4 mL. Similarly, the worst-case patient line volume of 84.1 mL may be used for medium/high feature sets 610.

In some embodiments, the accuracy adjustment may be based on a volume measurement error for measuring the amount of the fluid (for instance, dialysate) needed to completely fill the fluid system (for instance, to have the fluid system filled with fluid in the absence of air). For example, if the volume information, manufacturer specifications, and/or the like for the fluid system indicates that a volume of X mL (for instance, based on tubing length and diameter) is required to completely fill the fluid system, but actual measurements indicate that a volume of X+Y mL is required, then the accuracy adjustment may be Y mL (or a percentage, ratio, or other value based on Y mL). In various embodiments, the accuracy adjustment may be based on a plurality of measurements (for instance, a standard deviation or other construct based on a plurality of measurements).

Figure 7:
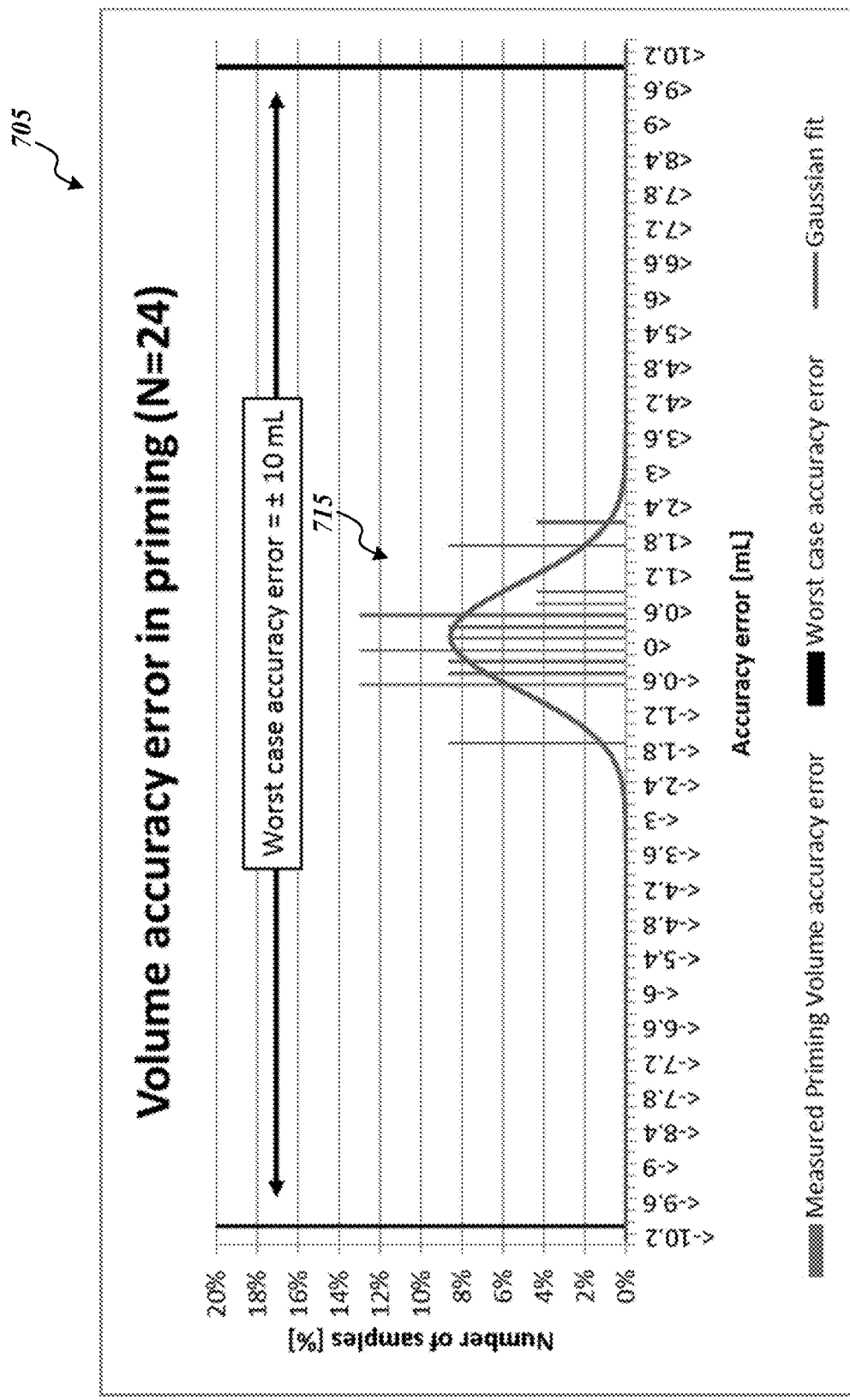
FIG. 7 illustrates exemplary accuracy adjustment determinations in accordance with the present disclosure.

FIG. 7 depicts accuracy adjustment for a fluid system according to some embodiments. As shown in graph 705 of FIG. 7, n=24 volume accuracy experiments were conducted for a fluid system. The worst-case accuracy adjustment or error based on the adjustment measurement information depicted in graph 705 is about +/−10 mL. In some embodiments, the accuracy adjustment may be determined based on a multiplier of a standard deviation or other construct of measurement errors (for example, bars 715 or based on bars 715). For example, the accuracy adjustment$_{max}$ may equal (multiplier)×(standard deviation). In the example depicted in FIG. 7, accuracy adjustment$_{max}$ may be determined by: (6)×(standard deviation)=+/−10 mL. In exemplary embodiments, the full accuracy adjustment (see, for example, FIG. 8) may be the difference between the highest accuracy error (10 mL) and the lowest accuracy error (−10 mL). For example, the full accuracy error for the example of graph 705 may be 10 mL−(−10 mL)=20 mL.

In various embodiments, a worst-case volume error may be determined based on the full accuracy adjustment and the full patient line error according to the following:

$$\text{worst-case volume error} = \sqrt{\left(\frac{\text{full accuracy error}}{2}\right)^2 + \left(\frac{\text{full patient line error}}{2}\right)^2}.\quad\text{Eq. 4}$$

Figure 8:
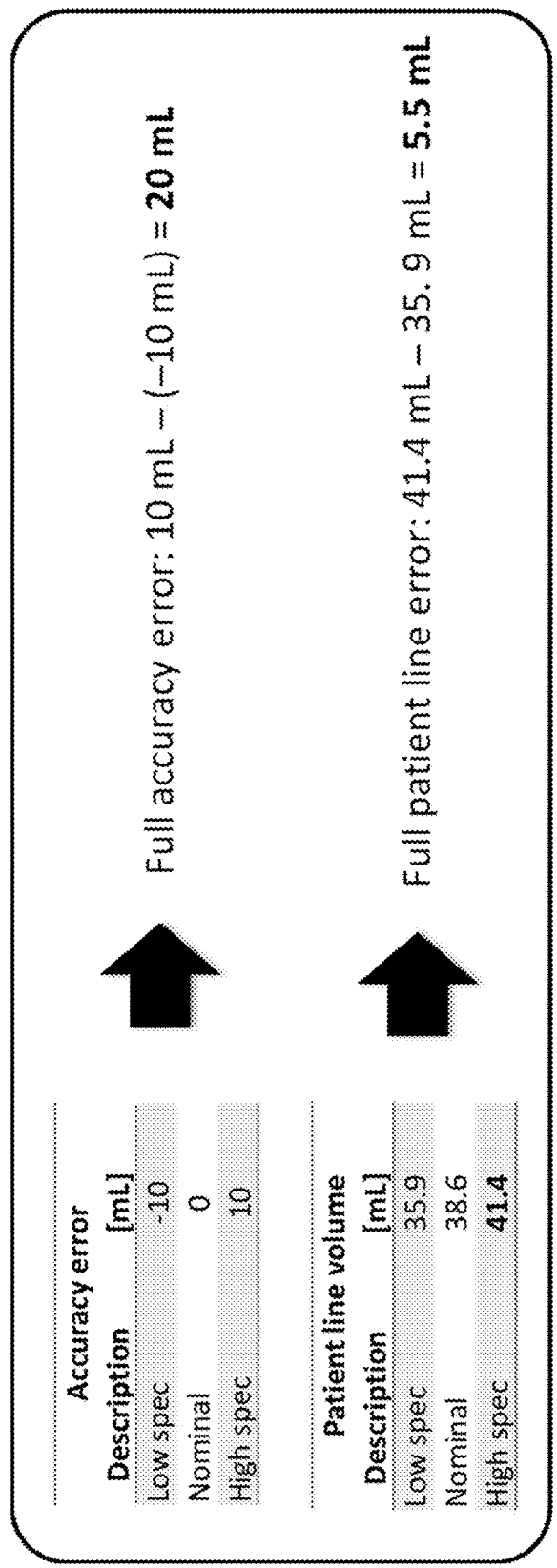
FIG. 8 illustrates exemplary worst-case volume error determinations in accordance with the present disclosure.

For example, the worst-case volume error for the example provided in FIG. 8 may be determined according to the following:

$$\text{worst-case volume error} = \sqrt{\left(\frac{20}{2}\right)^2 + \left(\frac{5.5}{2}\right)^2} = 10.3 \text{ mL}.$$

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic flow.

A logic flow may be implemented in software, firmware, hardware, or any combination thereof. In software and firmware embodiments, a logic flow may be implemented by computer executable instructions stored on a non-transitory computer readable medium or machine readable medium. The embodiments are not limited in this context.

Figure 9:
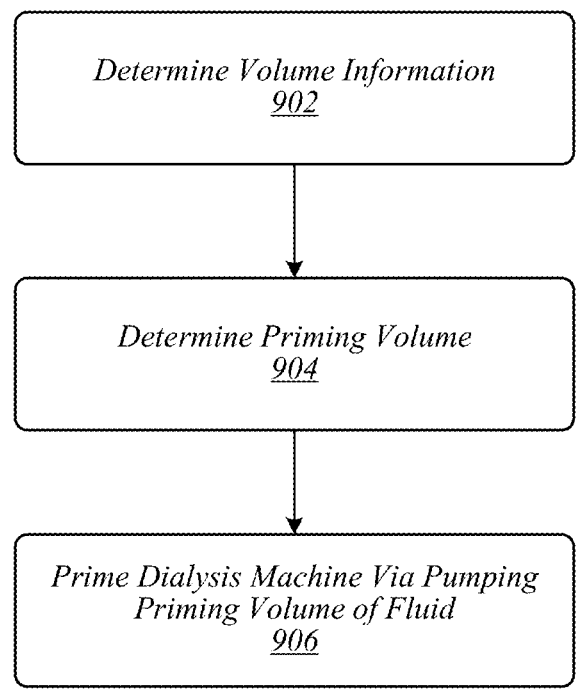
FIG. 9 illustrates a first logic flow in accordance with the present disclosure.

FIG. 9 illustrates an embodiment of a logic flow 900. The logic flow 900 may be representative of some or all of the operations executed by one or more embodiments described herein, such as dialysis machine 200, controller 305, and/or processor circuitry 520, and/or components thereof. In some embodiments, the logic flow 900 may be representative of some or all of the operations of executing a volume-based priming process.

The logic flow 900 may determine volume information at block 902. For example, processor 520 (for instance, via priming application 540) may determine volume information 534 including tubing information 550, system elements information 552, and accuracy adjustment information 554 for dialysis machine 200. In some embodiments, at least a portion of volume information 534 may be input by an operator of dialysis machine 200. For example, an operator may input a tubing length, tubing type (for instance, product A of manufacturer B), tubing dimensions, predetermined configuration, and/or the like. In various embodiments, at least a portion of volume information 534 may be automatically determined based on one or more factors, such as operator input, component identifiers, predefined configurations, and/or the like. For example, an operator may input that a "short" tubing set is being used and the priming logic 522 may determine the corresponding volume information 534 for a "short" tubing set. In another example, an operator may input that a tubing set of about 5 m is being used and the priming logic 522 may determine the corresponding volume information 534 for a 5 m tubing set.

At block 904, the logic flow 900 may determine a priming volume. For example, the processor 520 may access volume information 534 to determine the priming volume 560. In various embodiments, the priming volume 560 may be the worst-case volume, for instance, for a particular configuration or set of configurations, accounting for variations through the fluid system. Configurations may be categorized based on various characteristics including, without limitation, tubing length, tubing diameter, tubing manufacturer, a specific tubing product, tubing material, and/or the like, and/or any combinations thereof. For example, priming volume categories may be determined for a "short" tubing set, a "long" tubing set, and/or the like. Each tubing type (for instance, "short," "long," and/or the like) may be associated with various characteristics (or "feature sets"), such as inner dimension, outer dimension, and/or the like. The "short" tubing priming volume 560 may be generated for tubing of a certain length (or lengths) to be the worst-case for all feature sets for that length or category of length. For example, a "short" tubing volume 560 may be generated to prime tubing sets of a particular length (for instance, 3 m) or shorter for certain feature sets (for instance, a small feature set of a 1 mm inner diameter, a medium feature set of a 3 mm diameter, a large feature set of a 5 mm inner diameter, and/or the like).

In various embodiments, logic flow 900 may determine the priming volume 560 according to the equation (1). In various embodiments, the volume patient line$_{max}$ may include tubing information 550 for the volume of the patient tubing line and/or other fluid system components that need to be primed during the volume-based priming process. For example, in some embodiments, the volume patient line$_{max}$ may include the tubing of the fluid system. In another example, the volume patient line$_{max}$ may include the tubing and portions of a cartridge, such as a patient hub in the cartridge (for instance, about 2 mL, based on, for example, a hub volume of 1.83 mL and a PPS volume of 0.12 mL), if applicable.

In such embodiments, the priming volume 560 may be determined according to the following equation (2):

$$\text{priming volume} = \text{volume patient line}_{max} + \text{accuracy adjustment}_{max} - \text{volume non-primed elements.}$$

The logic flow 900 may prime the dialysis machine via pumping the priming volume of fluid through the fluid system at block 906. For example, the processor 520 may cause a pump (for instance, pump 350) of dialysis machine 200 to pump the priming volume 560 of fluid (for instance, dialysate) through the fluid system. In some embodiments, the entire fluid system of dialysis machine 200 may be primed with fluid. In various other embodiments, only fluid system components requiring priming (for instance, fluid system excluding non-primed elements) may be primed with fluid.

Figure 10:
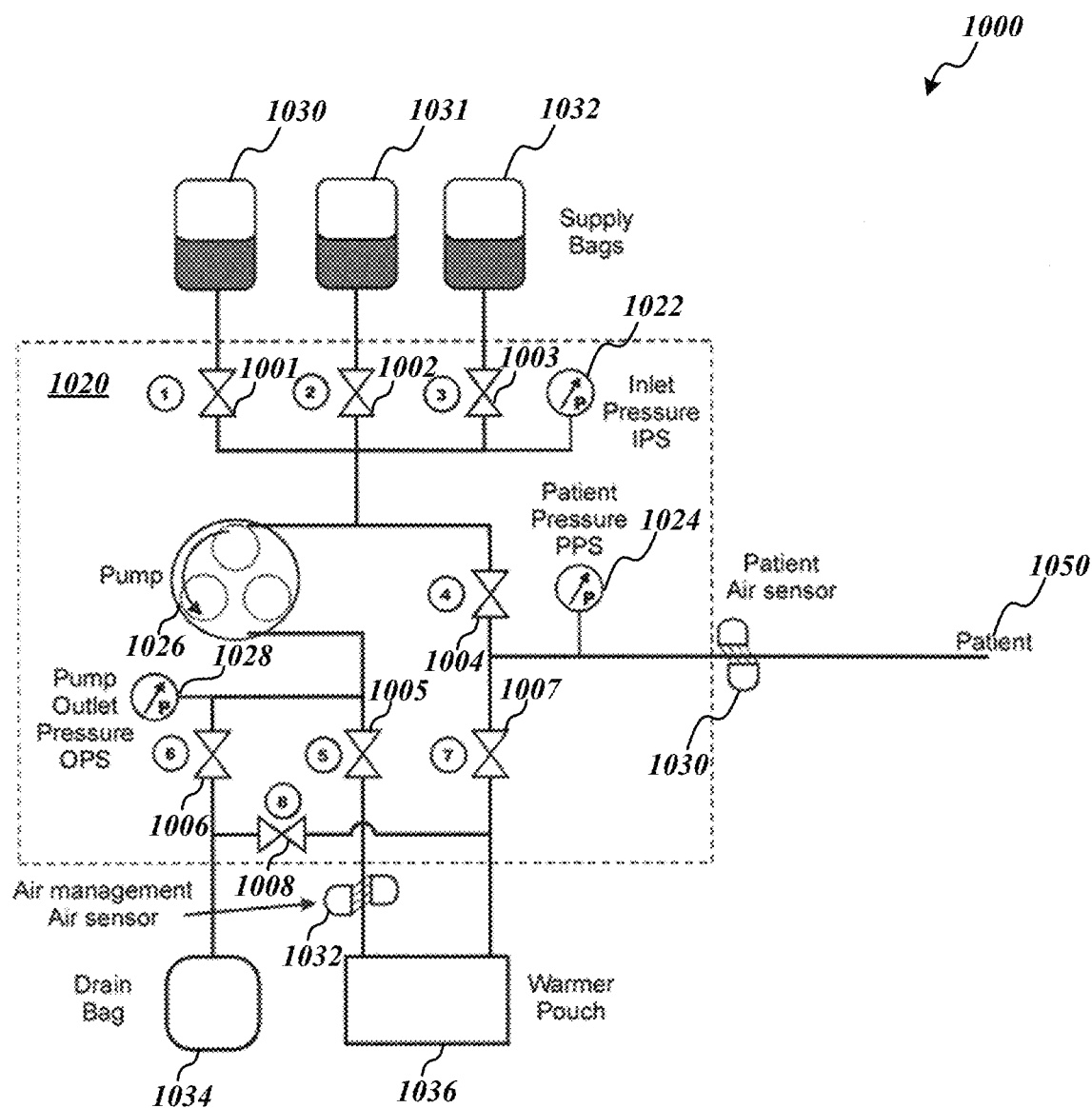
FIG. 10 illustrates an exemplary embodiment of a second dialysis system configured in accordance with the present disclosure.

FIG. 10 illustrates an exemplary embodiment of a dialysis system 1100 in accordance with the present disclosure. As shown in FIG. 10, the dialysis system 1000 may include a dialysis machine 1020 operative to facilitate dialysis of a patient 1050. In some embodiments, the dialysis machine 1020 may include a plurality of valves 1001-1008 operative to manage the movement of fluid within the dialysis machine 1020. A plurality of supply bags 1030-1032 may be arranged to supply fresh dialysate to the dialysis machine 1020. In various embodiments, the dialysis machine 1020 may be associated with various pressure sensors to determine the pressure of fluid within certain portions of the dialysis machine 1020, such as an inlet pressure sensor (IPS) 1022, a PPS 1024, and/or an OPS 1028. In exemplary embodiments, the dialysis machine 1020 may be associated with various air sensors, including a patient air sensor 1030 and/or an air management air sensor 1032. In some embodiments, a pump 1026 may be operative to pump fluid (i.e., dialysate) from the supply bags 1030-1032 throughout portions of the dialysis machine 1020 (for instance, depending on an open/close status of the valves 1001-1008). In various embodiments, the dialysis machine 1020 may be associated with a drain bag 1034 and/or a warmer pouch 1036.

Figure 11:
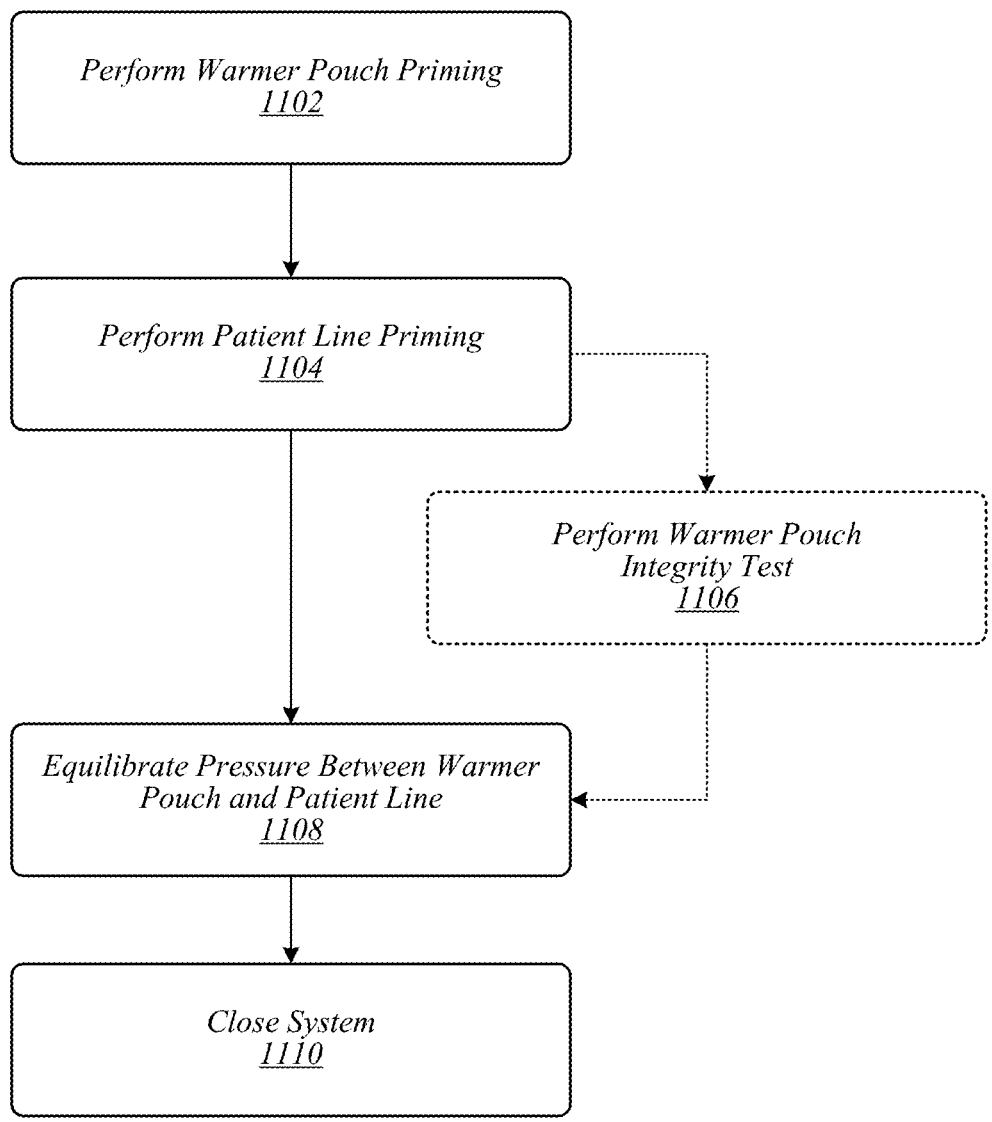
FIG. 11 illustrates a first logic flow in accordance with the present disclosure.

FIG. 11 illustrates an embodiment of a logic flow 1100. The logic flow 1100 may be representative of some or all of the operations executed by one or more embodiments described herein, such as dialysis machine 200, controller 305, processor 520, dialysis system 1000, and/or components thereof. In some embodiments, the logic flow 1100 may be representative of some or all of the operations of executing a volume-based priming process for a dialysis machine having a fluid warming system (for instance, see, in-line fluid warming system of FIG. 2).

The logic flow 1100 may perform warmer pouch priming at block 1102. For example, the controller 305 may cause a warmer pouch priming process to prime the warmer pouch 224. In various embodiments, in reference to FIG. 10, warmer pouch priming using solution from supply bag 1030 may use valves 1001, 1005, 1007, and/or 1008, solution from supply bag 1031 bag may use valves 1002, 1005, 1007, and/or 1008, an solution from supply bag 1032 may use valves 1003, 1005, 1007, and/or 1008. In some embodiments, a warmer pouch priming sequence may include opening a supply bag valve (i.e., valves 1001, 1002, or 1003) for at least one supply bag, valve 1005, and 1008 in order to prime the warmer pouch. In various embodiments, valve 1008 may be closed and value 1007 opened in order to prime a patient line. In exemplary embodiments, after warmer pouch priming, valve 1008 may be closed and valves 1001 and 1005 may be maintained in an open state. In some embodiments, the warmer pouch priming process may include or may be followed by one or more other processes (for instance, pressurization), tests, and/or the like. For example, an illustrative pressurization process may include the controller 305 may cause fluid to be pumped into the warmer pouch 224, pumping in a certain warmer pouch pressure (for instance, about 40 mbar outlet pressure sensor (OPS) (average)) with a warmer pouch maximum volume (for instance, about 50 mL) at a particular flow rate (for instance, a flow rate identical to a warmer pouch integrity test). In some embodiments, all of valves 1001-1008 may be closed following the pressurization process.

At block 1104, the logic flow 1100 may perform patient line priming. For example, the processor 520 may perform a volume-based priming process, such as according to the embodiment of logic flow 900 of FIG. 9. In some embodiments, in reference to FIG. 10, valves 1001 (or the supply bag valve for the corresponding supply bag), 1005, and 1007 may be opened. In various embodiments, for example, the volume-based priming process may include pumping a priming volume 560 of fluid at a particular flow rate (for instance, about 47.3 mL for a "low feature" tubing set or about 90.6 mL for a "medium/high" feature set at a flow rate of about 200 mL/m). The volume-based priming process for the dialysis machine 200 may have an occlusion limit, for instance, 340 mbar at peak (PPS). In some embodiments, in reference to FIG. 10, valve 1007 may be closed following a time period (for instance, about 15 seconds) following filling the patient line with the proscribed volume for the feature set at the proscribed flow rate.

The logic flow 1100 may optionally perform a warmer pouch integrity test at block 1106. For example, controller 305 may perform an integrity test for warmer pouch 224 (for instance, OPS to about 200 mbar), finishing with pumping in back pressure to 40 mbar on OPS.

At block 1108, the logic flow 1100 may equilibrate the pressure between the warmer pouch and the patient line. For example, controller 305 may actuate one or more valves to facilitate the equilibration of pressure between the warmer pouch 224 and the patient line (and/or remainder of the fluid system). In some embodiments, in reference to FIG. 10, to equilibrate pressure between the warmer pouch and the patient line, valve 1007 may be opened while valves 1001 (or the supply bag valve for the corresponding supply bag), 1005, and 1008 may be closed.

The logic flow 1100 may close the system at block 1110. For example, controller 305 may close all or substantially all valves to close off the fluid system of the dialysis machine 200. In another example, in reference to FIG. 10, valve 1007 may be closed, for instance, to prevent fluid flow into the patient line.

Figure 12:
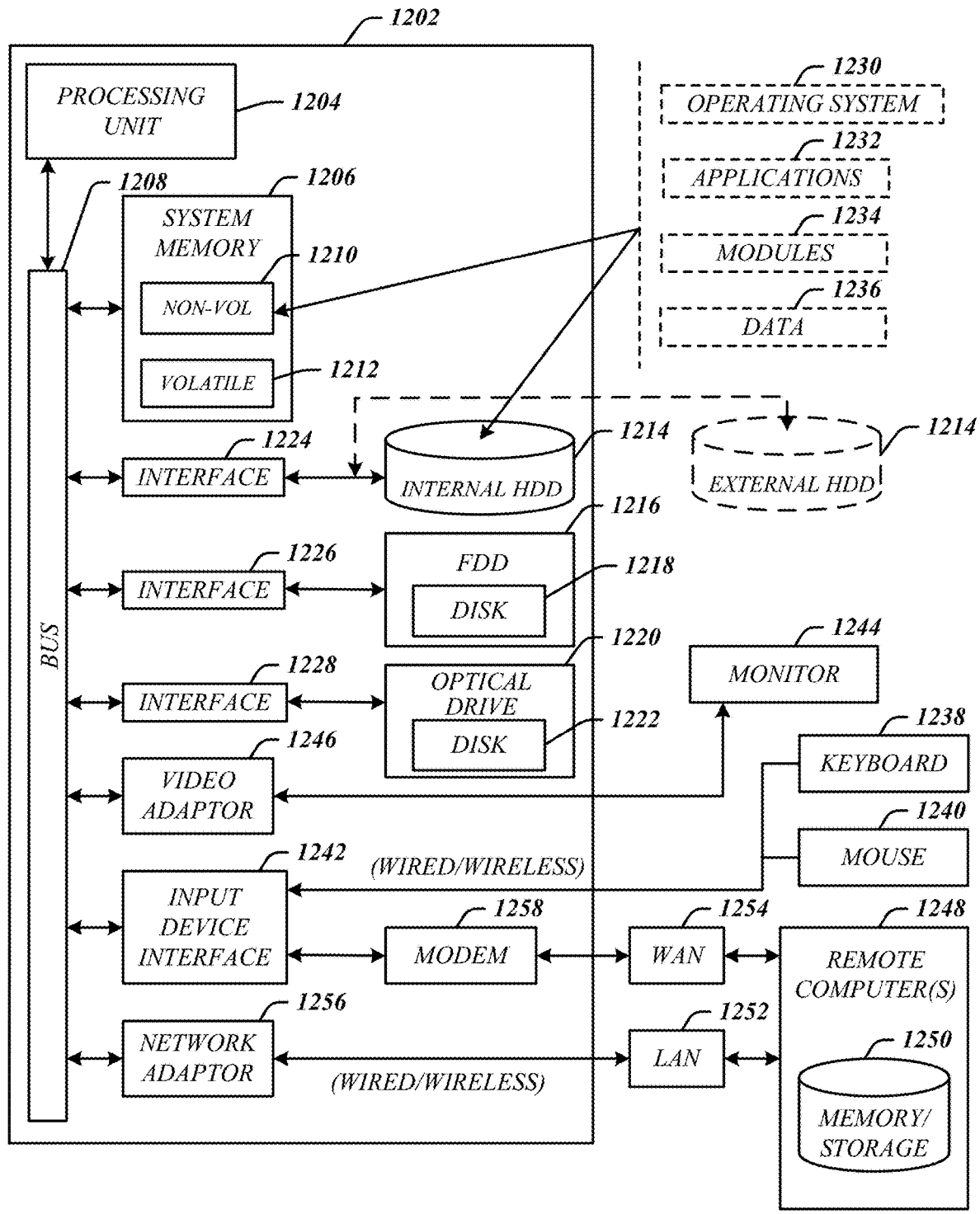
FIG. 12 illustrates an embodiment of a computing architecture in accordance with the present disclosure.

FIG. 12 illustrates an embodiment of an exemplary computing architecture 1200 suitable for implementing various embodiments as previously described. In various embodiments, the computing architecture 1200 may comprise or be implemented as part of an electronic device. In some embodiments, the computing architecture 1200 may be representative, for example, of dialysis machine 200, controller 305, and/or processor circuitry 520. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 1200. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1200 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1200.

As shown in FIG. 12, the computing architecture 1200 comprises a processing unit 1204, a system memory 1206 and a system bus 1208. The processing unit 1204 may be a commercially available processor and may include dual microprocessors, multi-core processors, and other multi-processor architectures.

The system bus 1208 provides an interface for system components including, but not limited to, the system memory 1206 to the processing unit 1204. The system bus 1208 can be any of several types of bus structure that may further interconnect to a memory bus (with or without a memory controller), a peripheral bus, and a local bus using any of a variety of commercially available bus architectures. Interface adapters may connect to the system bus 1208 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1206 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 12, the system memory 1206 can include non-volatile memory 1210 and/or volatile memory 1212. A basic input/output system (BIOS) can be stored in the non-volatile memory 1210.

The computer 1202 may include various types of computer-readable storage media in the form of one or more lower speed memory units, including an internal (or external) hard disk drive (HDD) 1214, a magnetic floppy disk drive (FDD) 1216 to read from or write to a removable magnetic disk 1211, and an optical disk drive 1220 to read from or write to a removable optical disk 1222 (e.g., a CD-ROM or DVD). The HDD 1214, FDD 1216 and optical disk drive 1220 can be connected to the system bus 1208 by a HDD interface 1224, an FDD interface 1226 and an optical drive interface 1228, respectively. The HDD interface 1224 for external drive implementations can include at least one or both of Universal Serial Bus (USB) and IEEE 1114 interface technologies.

The drives and associated computer-readable media provide volatile and/or nonvolatile storage of data, data structures, computer-executable instructions, and so forth. For example, a number of program modules can be stored in the drives and memory units 1210, 1212, including an operating system 1230, one or more application programs 1232, other program modules 1234, and program data 1236. In one embodiment, the one or more application programs 1232, other program modules 1234, and program data 1236 can include, for example, the various applications and/or components of apparatus 105, 205, 305, and/or 405.

A user can enter commands and information into the computer 1202 through one or more wired/wireless input devices, for example, a keyboard 1238 and a pointing device, such as a mouse 1240. These and other input devices are often connected to the processing unit 1204 through an input device interface 1242 that is coupled to the system bus 1208, but can be connected by other interfaces.

A monitor 1244 or other type of display device is also connected to the system bus 1208 via an interface, such as a video adaptor 1246. The monitor 1244 may be internal or external to the computer 1202. In addition to the monitor 1244, a computer typically includes other peripheral output devices, such as speakers, printers, and so forth.

The computer 1202 may operate in a networked environment using logical connections via wired and/or wireless communications to one or more remote computers, such as a remote computer 1248. The remote computer 1248 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1250 is illustrated. The logical connections depicted include wired/wireless connectivity to a local area network (LAN) 1252 and/or larger networks, for example, a wide area network (WAN) 1254. Such LAN and WAN networking environments are commonplace in offices and companies, and facilitate enterprise-wide computer networks, such as intranets, all of which may connect to a global communications network, for example, the Internet.

The computer 1202 is operable to communicate with wired and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysis machine, comprising:
   at least one processor;
   a memory coupled to the at least one processor, the memory comprising instructions that, when executed by the at least one processor, cause the at least one processor to perform a volume-based priming process for the dialysis machine, the volume-based priming process operative to:
   receive volume information associated with a fluid system of the dialysis machine, the volume information comprising:
   tubing information associated with a set of patient line tubing, and
   system element information associated with non-patient line tubing elements of the fluid system, and
   determine the priming volume to prime the fluid system with a fluid based on the volume information.

2. The dialysis machine of claim 1, further comprising a pump, wherein the volume-based priming process is operative to prime the fluid system by causing the pump to pump the priming volume of the fluid into the fluid system.

3. The dialysis machine of claim 1, the tubing information associated with a length and a diameter of the set of patient line tubing.

4. The dialysis machine of claim 1, the volume-based priming process operative to determine the tubing information based on an identifier of the set of patient line tubing.

5. The dialysis machine of claim 1, the volume-based priming process operative to:
   receive input indicating a predefined configuration of the fluid system, and
   determine at least one of the tubing information or the system element information based on the predefined configuration.

6. The dialysis machine of claim 1, the volume-based priming process operative to:
   determine a volume of non-primed elements of the fluid system, and
   determine the priming volume to exclude the volume of non-primed elements.

7. The dialysis machine of claim 1, the volume-based priming process operative to determine an accuracy adjustment volume associated with a volume measurement error for measuring a volume of the fluid required to fill the fluid system.

8. The dialysis machine of claim 7, the volume-based priming process operative to determine the priming volume according to:

priming volume=volume patient line+accuracy adjustment.

9. The dialysis machine of claim 1, the non-patient line tubing elements comprising at least one of a fluid container, a cartridge, a hub, or a pressure sensor.

10. The dialysis machine of claim 1, the priming volume comprising a maximum volume of fluid required to prime a configuration of the fluid system.

11. A method to prime a fluid system of a dialysis machine using a volume-based priming process, the method comprising:
receiving volume information associated with a fluid system of the dialysis machine, the volume information comprising:
tubing information associated with a set of patient line tubing, and
system element information associated with non-patient line tubing elements of the fluid system; and
determining the priming volume to prime the fluid system with a fluid based on the volume information.

12. The method of claim 11, comprising priming the fluid system by causing a pump to pump the priming volume of the fluid into the fluid system.

13. The method of claim 11, the tubing information associated with a length and a diameter of the set of patient line tubing.

14. The method of claim 11, comprising determining the tubing information based on an identifier of the set of patient line tubing.

15. The method of claim 11, comprising:
receiving input indicating a predefined configuration of the fluid system, and
determining at least one of the tubing information or the system element information based on the predefined configuration.

16. The method of claim 11, comprising:
determining a volume of non-primed elements of the fluid system, and
determining the priming volume to exclude the volume of non-primed elements.

17. The method of claim 11, comprising determining an accuracy adjustment volume associated with a volume measurement error for measuring a volume of the fluid required to fill the fluid system.

18. The method of claim 17, comprising determining the priming volume according to: priming volume=volume patient line+accuracy adjustment.

19. The method of claim 11, the non-patient line tubing elements comprising at least one of a fluid container, a cartridge, a hub, or a pressure sensor.

20. The method of claim 11, the priming volume comprising a maximum volume of fluid required to prime a configuration of the fluid system.

* * * * *